United States Patent
Wang et al.

(10) Patent No.: US 11,744,868 B1
(45) Date of Patent: Sep. 5, 2023

(54) INONOTUS OBLIQUUS DEXTRAN, PREPARATION METHOD AND APPLICATION THEREOF

(71) Applicant: Jilin Agricultural University, Changchun (CN)

(72) Inventors: Qi Wang, Changchun (CN); Yu Yang, Changchun (CN); Yang Liu, Changchun (CN); Ling Su, Changchun (CN)

(73) Assignee: JILIN AGRICULTURAL UNIVERSITY, Changchun (CN)

( * ) Notice: Subject to any disclaimer, the term of this patent is extended or adjusted under 35 U.S.C. 154(b) by 0 days.

(21) Appl. No.: 18/107,255

(22) Filed: Feb. 8, 2023

(30) Foreign Application Priority Data

Mar. 25, 2022 (CN) .......................... 202210305707.8

(51) Int. Cl.
| | | |
|---|---|---|
| *A61K 36/07* | (2006.01) | |
| *A61K 31/721* | (2006.01) | |
| *A61P 35/00* | (2006.01) | |
| *A61P 1/18* | (2006.01) | |

(52) U.S. Cl.
CPC ............ *A61K 36/07* (2013.01); *A61K 31/721* (2013.01); *A61P 1/18* (2018.01); *A61P 35/00* (2018.01); *A61K 2236/331* (2013.01); *A61K 2236/333* (2013.01); *A61K 2236/53* (2013.01)

(58) Field of Classification Search
None
See application file for complete search history.

(56) References Cited

U.S. PATENT DOCUMENTS

| | | | | |
|---|---|---|---|---|
| 2006/0013825 A1* | 1/2006 | Kristiansen | .......... | A61K 36/074 |
| | | | | 424/195.15 |
| 2008/0031892 A1* | 2/2008 | Kristiansen | ............ | A61K 36/07 |
| | | | | 514/2.7 |
| 2010/0086647 A1* | 4/2010 | Kristiansen | .......... | A23K 20/163 |
| | | | | 426/62 |

FOREIGN PATENT DOCUMENTS

| CN | 104004106 A | | 8/2014 |
|---|---|---|---|
| CN | 111228317 A | * | 6/2020 |

OTHER PUBLICATIONS

Weng Liang et al., Medicinal Fungi, Dec. 31, 2019, p. 61, 1st edition, China Light Industry Press, China.

Xiao Haipeng, CDR Handbook of Clinical Use, Jun. 30, 2020, p. 1124, 1st edition, China Pharmaceutical Science and Technology Press, China.

* cited by examiner

*Primary Examiner* — Michael Barker
*Assistant Examiner* — Randall O Winston
(74) *Attorney, Agent, or Firm* — WPAT, PC (57) ABSTRACT

Disclosed are an Inonotus Obliquus dextran, a preparation method and application thereof, and relates to the field of medicines. The dextran has a structural formula as follows:

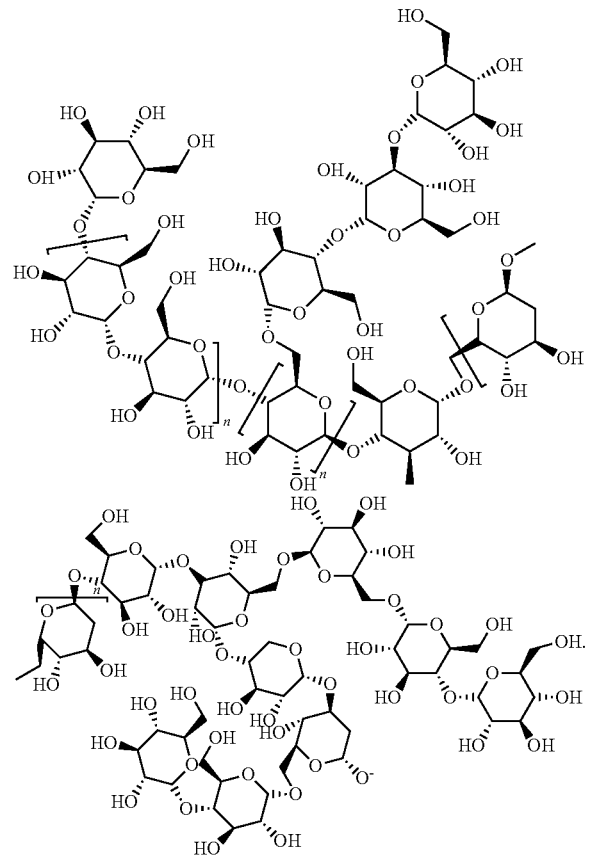

By optimizing the extraction and isolation process, the present disclosure obtains an Inonotus Obliquus dextran, which is structurally determined to be a new polysaccharide. The Inonotus Obliquus dextran prepared by the present disclosure is combined with gemcitabine hydrochloride to inhibit tumor cells with anti-tumor activity against pancreatic cancer, in addition to reduce the dosage of chemotherapeutic drugs as well as the adverse effects of chemotherapeutic drugs.

3 Claims, 10 Drawing Sheets

INONOTUS OBLIQUUS DEXTRAN, PREPARATION METHOD AND APPLICATION THEREOF

CROSS-REFERENCE TO RELATED APPLICATIONS

This application claims priority to Chinese Patent Application No. 202210305707.8, filed on Mar. 25, 2022, the contents of which are hereby incorporated by reference.

TECHNICAL FIELD

The present disclosure relates to the technical field of medicine, and in particular to an Inonotus Obliquus dextran, a preparation method and an application thereof.

BACKGROUND

Inonotus Obliquus, also known as chaga mushroom, is a fungus belonging to genus Inonotus, family Hymenochaetaceae, order Hymenochaetales, class Agaricomycetes and phylum Basidiomycota. Since the 16th century, the *Inonotus Obliquus* has been used for treating various diseases throughout the eastern Europe; after a long period of explorations, the *Inonotus Obliquus* has been proven to be effective in treating common chronic diseases such as diabetes and heart disease; and it is found to have good therapeutic potential for cancers of the digestive system based on a systematic study of the anti-cancer properties of the fungus conducted in Russia in 1955.

It is very difficult to diagnose pancreatic cancer, an exocrine adenocarcinoma of the pancreas, in its early stage. As one of the most common malignant tumors of the pancreas with a very high degree of malignancy, most cases of pancreatic cancer are found to be accompanied by distant metastases and/or invasion of surrounding organs, with a 5-year survival rate less than 5 percent (%). With an increasing incidence and mortality rate, pancreatic cancer has risen to the fourth leading cause of death among malignant tumors in China, and the incidence rate in urban areas is about two times higher than that in rural areas. Currently, there is no specific effective therapy for treating pancreatic cancer; it is possible for a patient to be cured provided with diagnosis and complete local excision as early as enough and followed by radiotherapy and chemotherapy, the 5-year survival rate is still not ideal, ranging from 15% to 40%. Study has shown that natural polysaccharides have good anti-tumor biological activity, and it is of great significance to develop polysaccharides with anti-tumor activity against pancreatic cancer from *Inonotus Obliquus* as well as to exploit this medicinal fungus.

SUMMARY

It is an objective of the present disclosure to provide an *Inonotus Obliquus* dextran, as well as its preparation method and application, so as to solve the problems existing in the prior art. The *Inonotus Obliquus* dextran obtained in the present disclosure is structurally novel with strong activity against pancreatic tumor and a high safety profile.

To achieve the above objective, the present disclosure provides the following technical schemes:

an *Inonotus Obliquus* dextran, where the dextran has a structural formula as follows:

The present disclosure also provides a method for preparing the *Inonotus Obliquus* dextran, including the following steps:

(1) extracting *Inonotus Obliquus* crude polysaccharide from *Inonotus Obliquus* fruiting body by a water-extraction and alcohol-precipitation method;

(2) deproteinizing the *Inonotus Obliquus* crude polysaccharide in step (1) by solvent extraction, followed by separation of components with molecular weight above 3,500 Dalton (Da) by dialysis to obtain a deproteinized crude sugar;

(3) purifying the deproteinized crude sugar by a DEAE-52 (Diethylaminoethyl) cellulose column to obtain purified *Inonotus Obliquus* polysaccharide; and (4) placing the purified *Inonotus Obliquus* polysaccharide on a Sephadex G-100 gel column and eluting it with distilled water at a controlled flow rate of 0.5 milliliter per minute (mL/min) to obtain the *Inonotus Obliquus* dextran.

Optionally, the water-extraction and alcohol-precipitation method in step (1) specifically includes: leaching *Inonotus Obliquus* fruiting body with deionized water to obtain a leaching solution, concentrating the leaching solution, adding ethanol to obtain *Inonotus Obliquus* crude polysaccharide by precipitation.

Optionally, the solvent extraction in step (2) uses Sevage reagent, prepared with n-butanol and chloroform in a volume ratio of 1:4.

Optionally, the purifying in step (3) specifically includes: dissolving the deproteinized crude sugar in water, followed by loading onto a DEAE-52 cellulose chromatographic column; then performing fractional elution with distilled water, 0.05 mole per liter (mol/L) NaCl, 0.1 mol/L NaCl and 0.2 mol/L NaCl respectively under a controlled flow rate of 1.0 mL/min, separately collecting eluents and combining polysaccharide elution sites to obtain purified *Inonotus Obliquus* polysaccharide.

The present disclosure also provides a composition for treating tumors, where the composition includes gemcitabine hydrochloride and the *Inonotus Obliquus* dextran.

Optionally, the tumors include human pancreatic cancer.

The present disclosure also provides an application of the *Inonotus Obliquus* dextran or the composition in preparing drugs for treating tumors.

Optionally, the tumors include the human pancreatic cancer.

The present disclosure achieves the following technical effects:

through extensive experiments, the extraction and isolation process is optimized, where crude polysaccharide is firstly obtained by the water-extraction and alcohol-precipitation method, then the crude polysaccharide is deproteinated and subjected to purification by DEAE-52 cellulose resin and Sephadex G-100 gel resin in combination to produce an *Inonotus Obliquus* dextran of high purity, which is structurally determined to be a new polysaccharide;

it has been proved after anti-tumor experiments that the *Inonotus Obliquus* dextran provided by the present disclosure has good anti-tumor activity against pancreatic cancer and is safe with no toxic side effects; the *Inonotus Obliquus* dextran can be prepared into drugs in various dosage forms with accessible and pharmaceutically acceptable carriers for easy clinical administration; and gemcitabine hydrochloride in combination with *Inonotus Obliquus* dextran prepared by the present disclosure has a synergistic effect with superior inhibition effect on tumors, achieving reduced dosage of chemotherapeutic drugs as well as alleviated adverse reaction of chemotherapeutic drugs as treating tumors.

BRIEF DESCRIPTION OF THE DRAWINGS

For a clearer illustration of the technical schemes in the embodiments of the disclosure or in the prior art, a brief description of the accompanying drawings to be used in the embodiments will be given below. It is obvious that the accompanying drawings in the following description are only some embodiments of the disclosure, and that other accompanying drawings may be obtained based on these drawings without any creative effort on the part of a person of ordinary skill in the art.

DETAILED DESCRIPTION OF THE EMBODIMENTS

Now various exemplary embodiments of the present disclosure are described in detail. This detailed description should not be taken as a limitation of the present disclosure, but should be understood as a rather detailed description of some aspects, characteristics and embodiments of the present disclosure.

It should be understood that the terms mentioned in the present disclosure are only used to describe specific embodiments, and are not used to limit the present disclosure. In addition, for the numerical range in the present disclosure, it should be understood that each intermediate value between the upper limit and the lower limit of the range is also specifically disclosed. Any stated value or intermediate value within the stated range, and any other stated value or intermediate value within the stated range are also included in the present disclosure. The upper and lower limits of these smaller ranges may be independently included or excluded from the range.

Unless otherwise stated, all technical and scientific terms used herein have the same meanings commonly understood by those of ordinary skill in the field to which this disclosure relates. Although the present disclosure only describes preferred methods and materials, any methods and materials similar or equivalent to those described herein may be used in the practice or testing of the present disclosure. All documents mentioned in this specification are incorporated by reference to disclose and describe the methods and/or materials related to the documents. In case of conflict with any incorporated documents, the contents of this specification shall prevail.

Without departing from the scope or spirit of the present disclosure, it is obvious to those skilled in the art that many modifications and changes can be made to the specific embodiments of the present specification. Other embodiments obtained from the description of the present disclosure will be obvious to the skilled person. The description and embodiment of that disclosure are only exemplary.

As used in this paper, the terms "comprising", "including", "having" and "containing" are all open terms, meaning including but not limited to.

Embodiment 1

1. Preparation of *Inonotus Obliquus* Polysaccharide
The polysaccharide is prepared as follows:
(1) Extraction of Crude Polysaccharide 300 grams (g) of *Inonotus Obliquus* are added into purified water of 7.5 liters (L) according to a solid-liquid ratio of 1:25, followed by extraction by maceration at 95 degree Celsius (° C.) for 3 times, each time is carried out for 6 hours (h) and followed by filtration; then the filtrates are combined to subjected to rotary evaporation at 95° C. to be concentrated to 2 L, followed by adding with absolute ethanol until the ethanol reaches a concentration of 75 percent (%), and standing at 4° C. for 12 h to obtain precipitate by filtration, and the *Inonotus Obliquus* crude polysaccharide is obtained after freeze-drying the precipitate;

(2) Deproteinization of Crude Polysaccharide the crude polysaccharide of *Inonotus Obliquus* prepared in step (1) is dissolved in 1.5 L of pure water, and added with Sevage reagent of 1/3 volume (by volume ratio, n-butanol:chloroform=1:4), followed by shaking in a horizontal shaker for 6 h and stood in a separatory funnel for another 6 h, then a supernatant, i.e. polysaccharide solution is obtained; the above method for deproteinization is repeated again until a bottom phase of the separatory funnel is transparent, followed by rotary evaporation to concentrate the solution; the concentrated solution is then dialyzed to retain components with a molecular weight of 3,500 Dalton (Da) or more, and a deproteinized crude polysaccharide solution is obtained;

(3) DEAE-52 Cellulose Column Chromatography the crude polysaccharide solution prepared in step (2) is freeze-dried into solid, then 20 milligrams (mg) of the solid is dissolved in water and load onto a DEAE-52 cellulose chromatographic column for purification, followed by fractional elution of distilled water, 0.05 mole per liter (mol/L) NaCl, 0.05 mol/L NaCl, 0.1 mol/L NaCl, 0.2 mol/L NaCl while controlling the flow rate at 1.0 milliliter per minute (mL/min); the eluents are separately collected, the polysaccharide sites are subjected to tracking detection by the sulphuric acid-phenol method and the polysaccharide elution sites are combined to obtain a purified *Inonotus Obliquus* polysaccharide;

(4) Sephadex G-100 gel column chromatography the *Inonotus Obliquus* polysaccharide purified by DEAE-52 cellulose chromatographic column in step (3) is applied to a Sephadex G-100 gel column and eluted with distilled water under a controlled flow rate of 0.5 mL/min, then sulfuric acid-phenol method is used again for tracking detection to obtain a refined *Inonotus Obliquus* polysaccharide, which is numbered as IOP1-1;

2. Structure Analysis of *Inonotus Obliquus* Polysaccharide (1) Infrared Analysis of *Inonotus Obliquus* Polysaccharide

Figure 1:
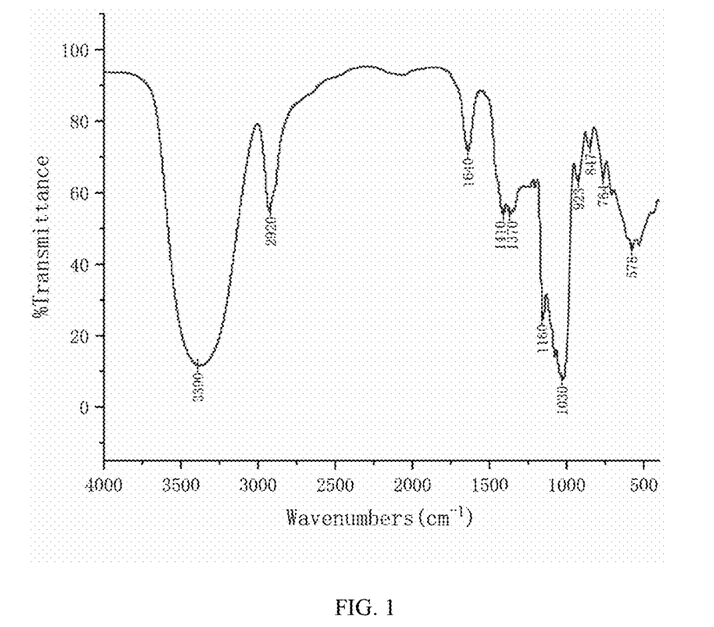
FIG. 1 shows an infrared spectrum of *Inonotus Obliquus* polysaccharide prepared in Embodiment 1.

*Inonotus Obliquus* polysaccharide IOP1-1 (1.8 mg) prepared by "1. Preparation of *Inonotus Obliquus* polysaccharide" is compressed with 190 mg of potassium bromide (KBr) and scanned in a range of 4,000-400 centimeters$^{-1}$ (cm$^{-1}$); as can be seen from FIG. 1, the peak at 3,390 cm$^{-1}$ absorption in the infrared spectrum indicates that the sugar chains have inter- and intra-molecular hydrogen bonds, which are also assigned as O—H stretching vibrations; the peak at 2,920 cm$^{-1}$ represents the asymmetric absorption of C—H; there is no glucuronic acid absorption near 1,730 cm$^{-1}$, suggesting that IOP1-1 might be a neutral polysaccharide; the peaks observed at 1,640 cm$^{-1}$ and 1,410 cm$^{-1}$ are attributed to the asymmetric and symmetric stretching vibrations of C—O, respectively; moreover, 1,200 to 1,000 cm$^{-1}$ is the fingerprint area for carbohydrates, with peaks at 1,160 cm$^{-1}$ and 1,030 cm$^{-1}$ being characterization of C—O—H and C—O—C stretching vibrations respectively, and the peaks at 923 cm$^{-1}$ and 847 cm$^{-1}$ indicate that *Inonotus Obliquus* polysaccharide contains β- and α-linked glycosyl residues; the above data represent the characteristic absorption peaks of this polysaccharide;

(2) Determination of Molecular Weight of *Inonotus Obliquus* Polysaccharide (2.1) chromatographic conditions: chromatographic column: Shodex OH-pak SB-805, 804 and 803 gel columns in series (8×300 millimeter (mm)); flow rate: 0.4 mL/min, column temperature: 45° C.; sample volume: 100 Microliters (μL); detector: DAWN HELEOS-II laser photometer (He—Ne laser, lambda λ=663.7 nano-meter (nm));

(2.2) Determination of Polysaccharide Molecular Weight

SEC-MALLS-RI method is used to measure the homogeneity and molecular weight (Mw) of polysaccharide components; the concentration of *Inonotus Obliquus* polysaccharide in 0.1 mole (M) NaNO$_3$ aqueous solution containing 0.02% NaNO$_3$ is 1 mg/mL; the aqueous solution is filtered by a filter with a pore size of 0.45 micrometre (μm), and Mw is calculated to be Mw=6.886 Kilodalton (kDa) according to the following formula:

$$\frac{K_c}{R_\theta} = \frac{1}{M_W}\left(1 + \frac{16\pi^2 n^2}{3\lambda_0^2} <s^2> z \sin^2\left(\frac{\theta}{2}\right)\right) + 2A_2c + \ldots, K = \frac{4\pi^2 n^2}{N_A \lambda_0^4}\left(\frac{dn}{dc}\right)^2,$$

where n is the refractive index of the solvent, K is the optical constant, $\lambda_0$ is the laser wavelength in vacuum, $N_A$ is the avogadro constant, $R_\theta$ is Rayleigh ratio, $A_2$ is the second virial coefficient, c is the mass concentration, and do/dc is the refractive index increment;

(3) Monosaccharide Composition of Polysaccharide (3.1) chromatographic conditions: chromatography system: ThermoICS5000 ion chromatography system; liquid chromatographic column: Dionex™ CarboPac™PA20 (150*3.0 mm, 10 μm); injection volume: 5 μL; mobile phase A: 0.1 M NaOH; mobile phase B: 0.1 M NaOH, 0.2 M NaAc; flow rate: 0.5 mL/min; column temperature: 30° C.; elution gradient: 0 min phase A/phase B (95:5, Volume to Volume, V/V), 30 min phase A/phase B (80:20, V/V), 30.1 min phase A/phase B (60:40, V/V), 45 min phase A/phase B (60:40, V/V), 45.1 min phase A/phase B (95:5, V/V) and 60 min phase A/phase B (95:5, V/V);

(3.2) Monosaccharide Composition of Polysaccharide fucose, rhamnose, arabinose, galactose, dextrose, xylose, mannose, fructose, ribose, galacturonic acid, glucuronic acid, mannuronic acid and guluronic acid are selected as monosaccharide standards; a clean vial is weighed accurately with 5 mg of *Inonotus Obliquus* polysaccharide, followed by adding with 1 mL 2 M trifluoroacetic (TFA) acid solution and heating at 105° C. for 6 h; then nitrogen is introduced to blow dry the solution; methanol is added to clean the solution, and the solution is blow-dried again and the methanol cleaning is carried out for 2-3 times; sterile water is added for dissolving, and the solution is transferred to chromatographic bottle for detection, with results showing that the polysaccharide of *Inonotus Obliquus* is a dextran composed of dextrose;

(4) Scanning Electron Microscope (SEM) Observation

Figure 2:
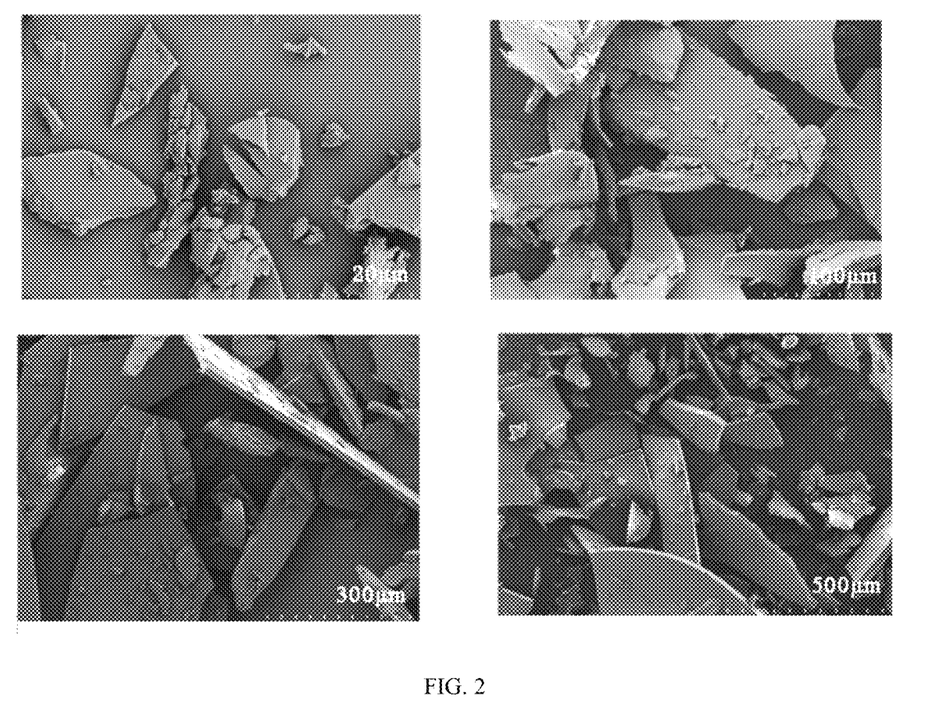
FIG. 2 illustrates scanning electron microscope images of *Inonotus Obliquus* polysaccharide prepared in Embodiment 1 at 20 micrometre (μm), 100 μm, 300 μm and 500 μm respectively.
Figure 3:
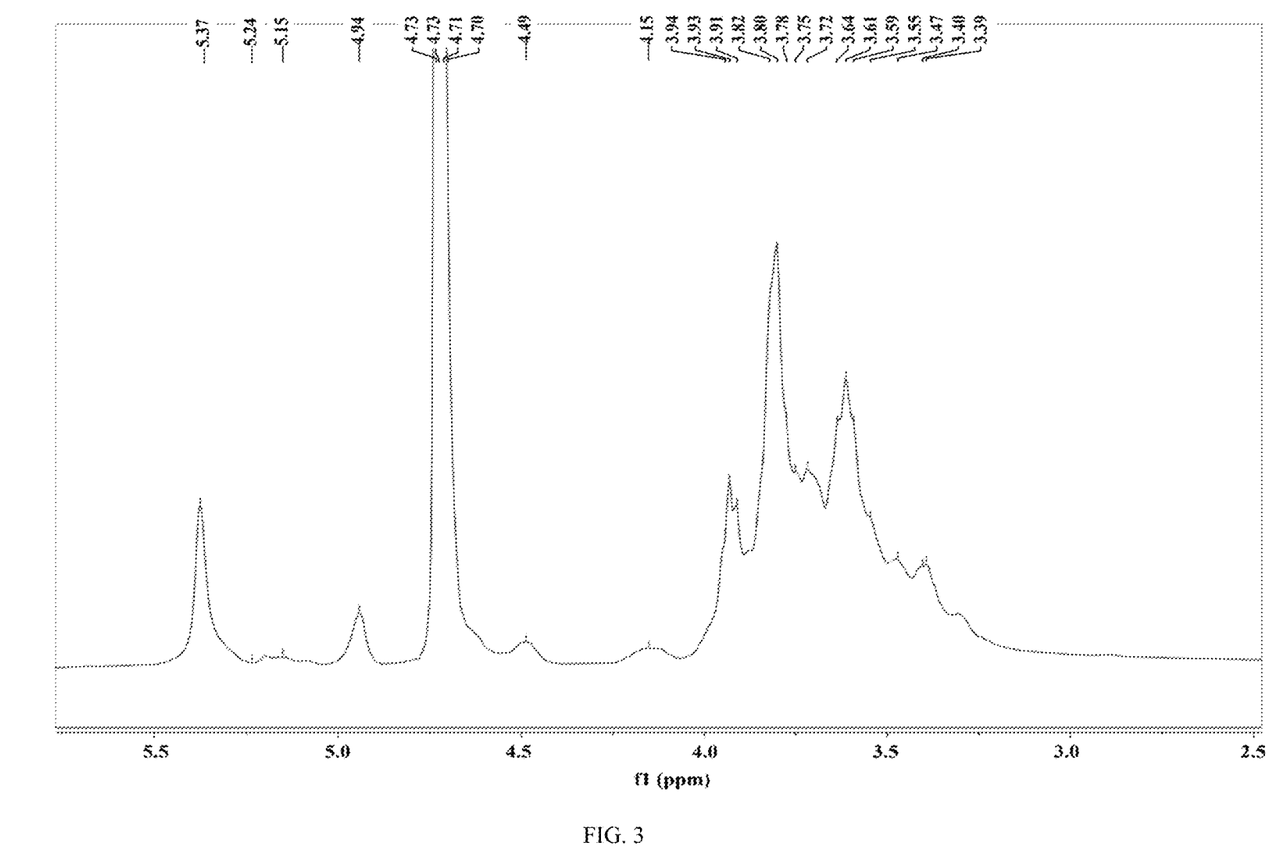
FIG. 3 shows a $^1$H nuclear magnetic resonance (NMR) spectrum of *Inonotus Obliquus* polysaccharide prepared in Embodiment 1.
Figure 4:
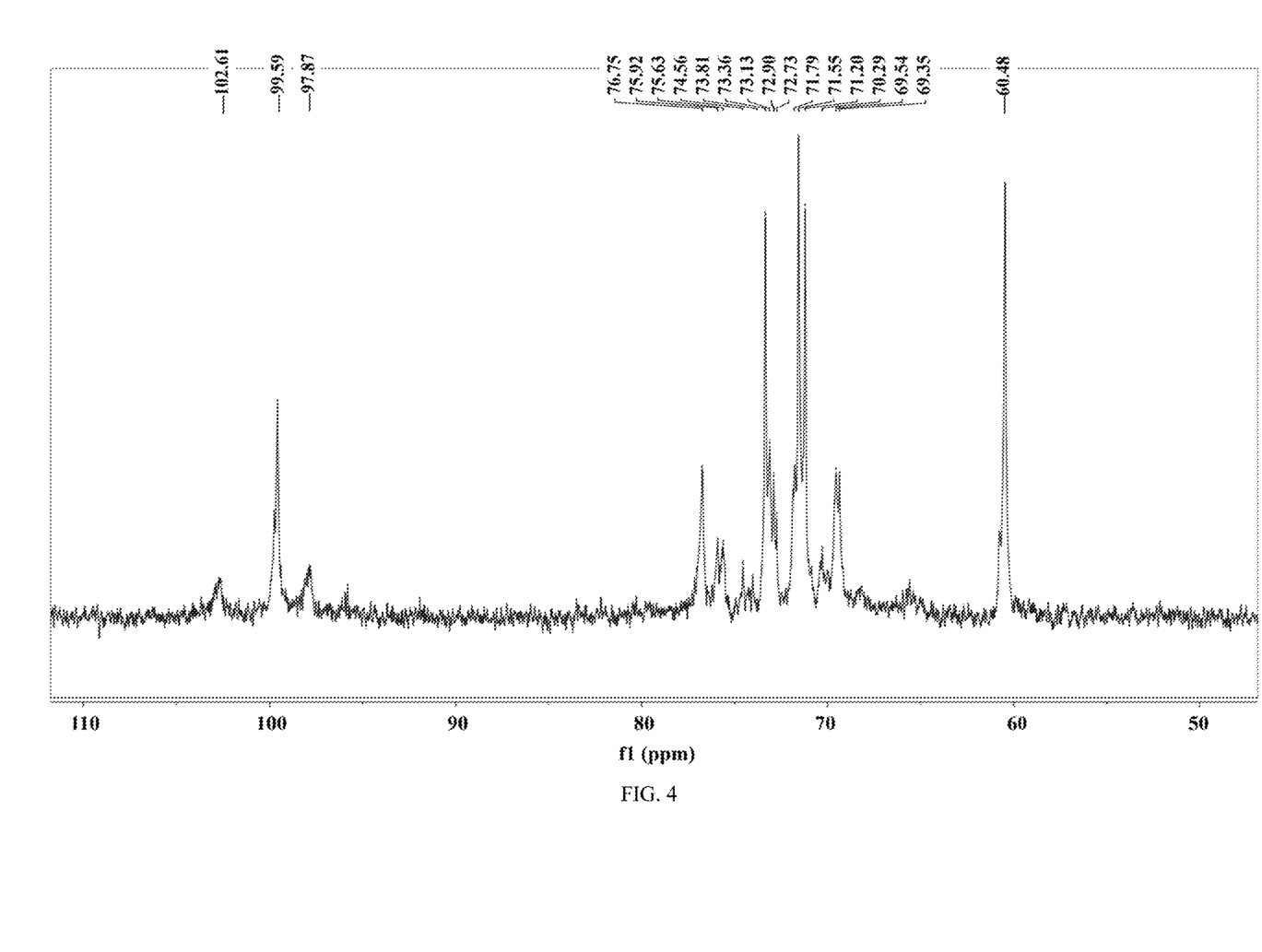
FIG. 4 shows a $^{13}$C NMR spectrum of *Inonotus Obliquus* polysaccharide prepared in Embodiment 1.
Figure 5:
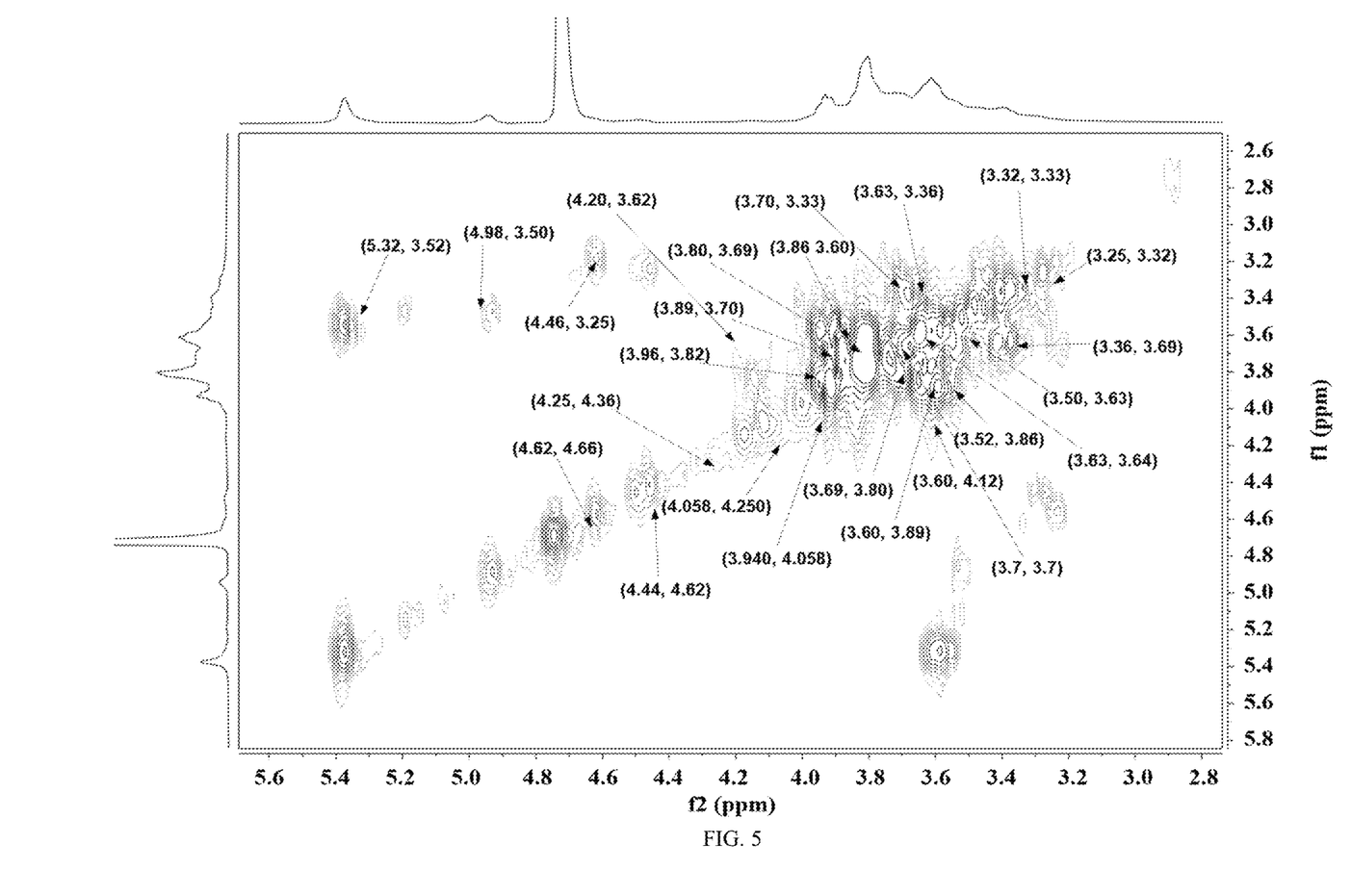
FIG. 5 shows a two dimensional (2D) correlation spectroscopy (COSY) NMR spectrum of *Inonotus Obliquus* polysaccharide prepared in Embodiment 1.
Figure 6:
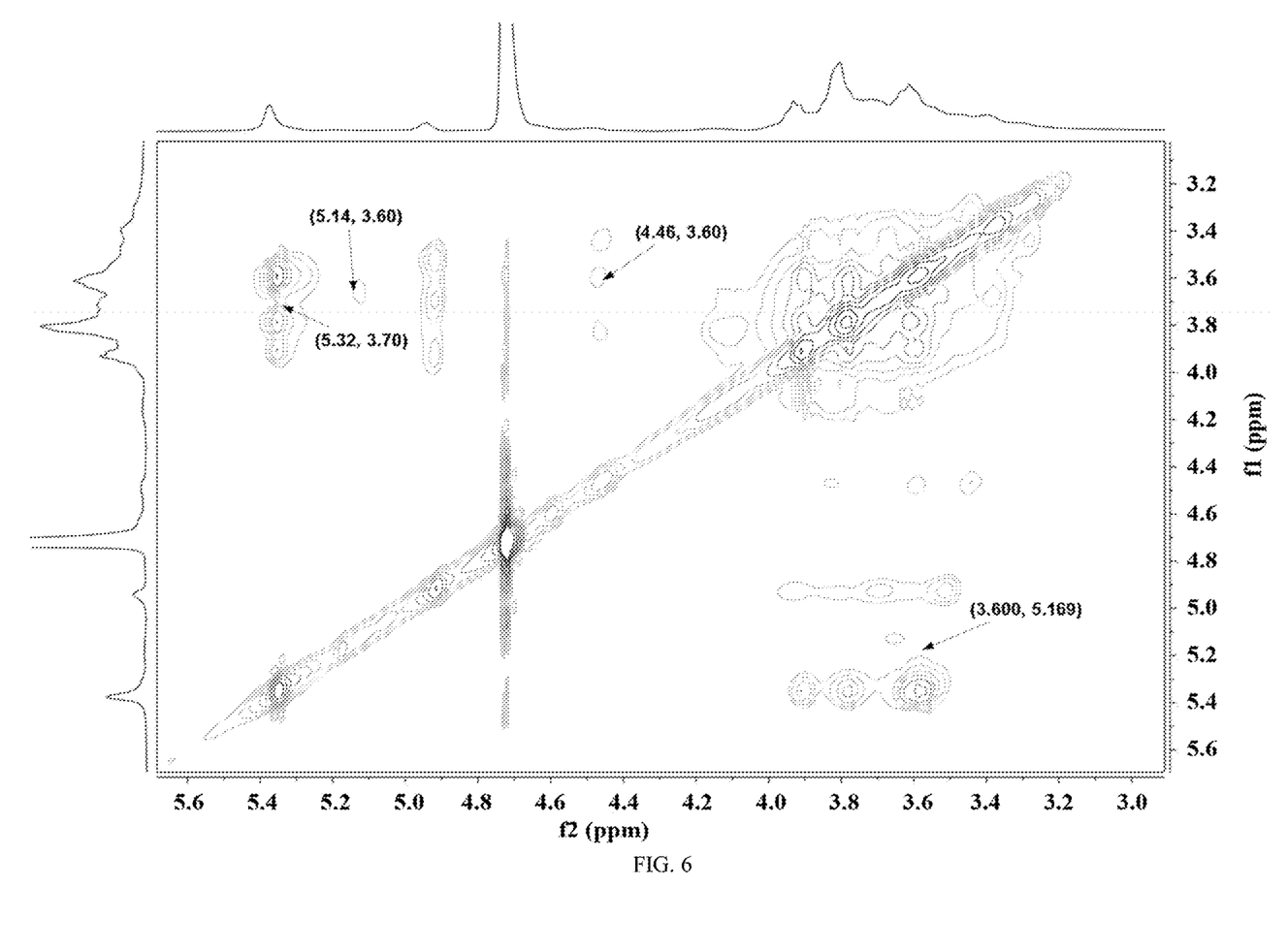
FIG. 6 shows a 2D nuclear overhauser effect spectroscopy (NOESY) NMR spectrum of *Inonotus Obliquus* polysaccharide prepared in Embodiment 1.
Figure 7:
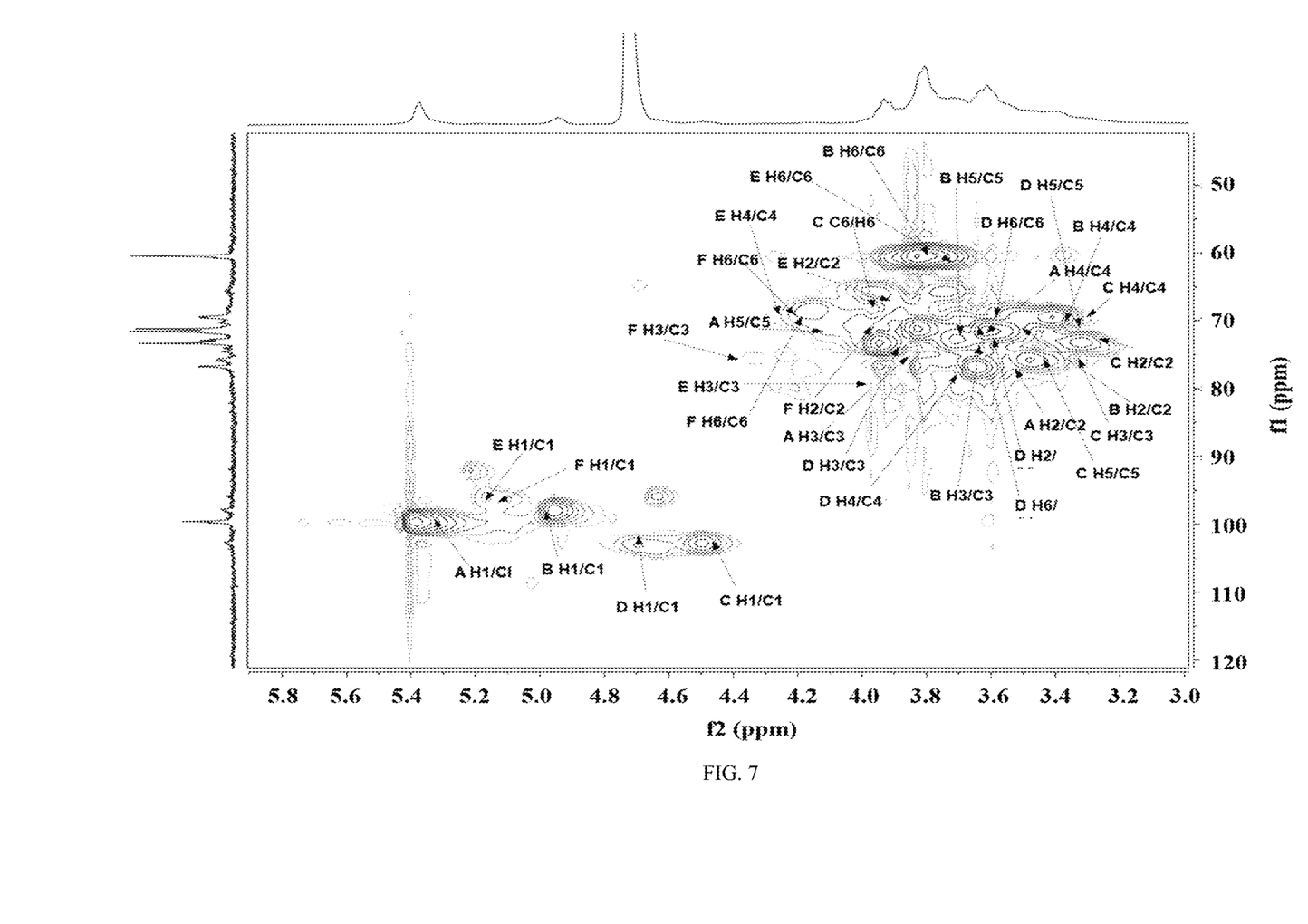
FIG. 7 shows a 2D Heteronuclear Single Quantum Coherence (HSQC) NMR spectrum of *Inonotus Obliquus* polysaccharide prepared in Embodiment 1.
Figure 8:
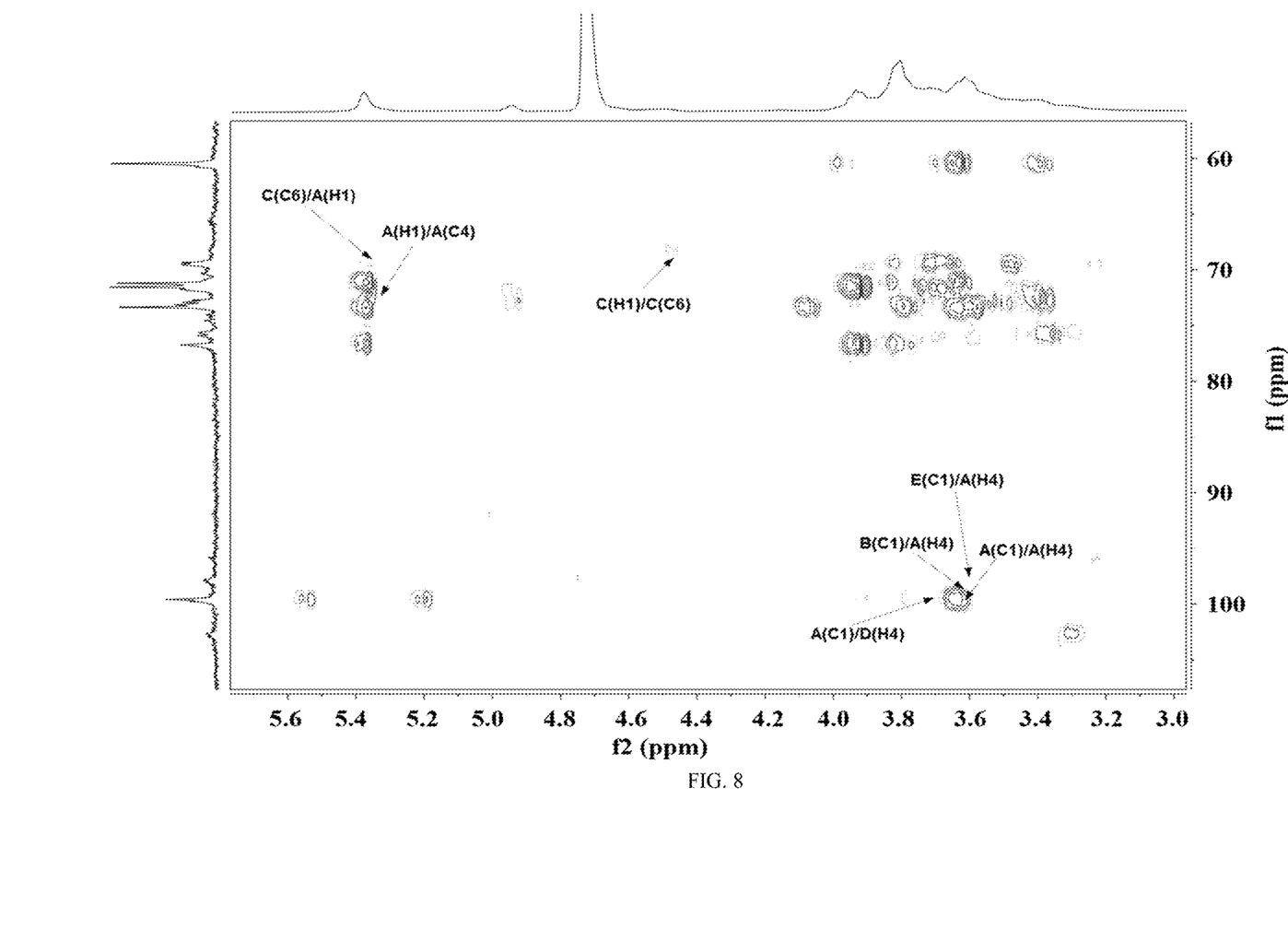
FIG. 8 shows a 2D Heteronuclear Multiple Bond Correlation (HMBC) NMR spectrum of *Inonotus Obliquus* polysaccharide prepared in Embodiment 1.

*Inonotus Obliquus* polysaccharide is attached to a conductive double sided adhesive carbon tape and subjected to gold spraying on a sample table of an ion sputtering instrument for about 30 seconds (s); the prepared sample is put on the sample table to be observed in terms of morphology by SEM at different scaling times, and the SEM image of the polysaccharide is shown in FIG. 2;

(5) Methylation Analysis methylation method:

① the sample of 10 mg is dissolved in 1 mL of sterile water and added with 1 mL of 100 mg/mL carbodiimide, followed by continuously stirring for 2 h and adding with 1 mL imidazole of 2 M; then the solution is divided into two parts equally, including: adding 1 mL sodium borohydride or 1 mL NaBD$_4$, both of which are 30 mg/mL, and waiting for 3 h; finally, glacial acetic acid of 100 μL is added to stop the reaction; and the sample is freeze-dried after dialyzing for 48 h and methylation;

② the sample is dissolved in 500 μL dimethyl sulphoxide (DMSO), followed by incubation for 30 min after adding 1 mg sodium hydroxide and reaction for 1 h with 50 μL methyl iodide; then the reacted sample is extracted with 1 mL of water and 2 mL of dichloromethane for 3 times, and the relatively phases are collected; the product is hydrolyzed with 2 M TFA at 121° C. for 1.5 h and dried at 30° C.; then 50 μL 1 M NaBD$_4$ and 50 μL 2 M ammonia are added for incubation at room temperature for 2.5 h after mixing well; 20 μL acetic acid is added to stop the reaction, and nitrogen is used for drying, followed by washing twice with 250 μL methanol and drying again;

③ 250 μL of cis-hydride is immediately added after drying and mixing well, followed by reaction at 100° C. for 2.5 h; then 1 mL water is added and stood for 10 min; finally, 500 μL dichloromethane is added and mixed well, and the sample is subjected to centrifuge with water phase being discarded; the water washing is repeated for 3 times, and the dichloromethane phase is taken from the lower layer for testing on the machine;

Gas Chromatography/Mass Spectrometry (GC/MS) conditions: Agilent gas chromatography system is adopted in the chromatographic system, with the injection volume of 1 μL, the split ratio of 10:1 and the carrier gas of high purity helium; the initial temperature of the column oven is held at 140° C. for 2.0 min and is ramped up to 230° C. in a 3° C./min program and held for 3 min;

the results of methylation assay show that the components of *Inonotus Obliquus* polysaccharide extracted and separated by this method are t-Glc(p), 3-Glc(p), 2-Glc(p), 6-Glc(p), 4-Glc(p), 3,4-Glc(p), 2,3-Glc(p), 2,4-Glc(p), 3,6-Glc(p), 4,6-Glc(p), 2,6-Glc(p) and 3,4,6-Glc(p), and the above units are in a molar ratio of 23.3:3.0:2.6:14.6:41.4:1.6:0.8:1.7:2.9:5.4:2.2:0.6;

(6) One-Dimensional and Two-Dimensional (2D) Spectrum Analysis of *Inonotus Obliquus* Polysaccharide a proper amount of purified polysaccharide is completely dissolved with 500 μL deuterium oxide (D2O) to prepare a solution with a concentration of greater than or equal to 30 mg/mL, and the solution is transferred to a nuclear magnetic tube (3.5-4 cm); $^1$H (FIG. 3), $^{13}$C (FIG. 4) and 2D nuclear magnetic resonance (NMR) spectra (FIG. 5 for correlation spectroscopy (COSY), FIG. 6 for nuclear overhauser effect spectroscopy (NOESY), FIG. 7 for heteronuclear single quantum coherence (HSQC) spectroscopy and FIG. 8 for heteronuclear multiple bond correlation (HMBC)) with high resolution are recorded at room temperature of 25° C. using Bruker 500 MHz jet apparatus, where the signals δ4.87, 4.8, 4.77, 4.63 in FIG. 3 and δ102.82, 101.29 in FIG. 4 are the signals of the heteroheaded proton and heteroheaded carbon of the polysaccharide, respectively; with reference to the methylation results, infrared analysis results and literature, for example, the signal δ99.51/3.60 can be attributed to →4)-α-D-Glcp-(1→; δ99.51/3.63 can be attributed to →4)-α-D-Glcp-(1→ and →4,6)-13-D-GlcpA-(1→; δ99.51/3.33 can be attributed to →4)-α-D-Glcp-(1→ and →6)-β-D-Glcp-(1→; δ99.51/4.20 can be attributed to →4)-α-D-Glcp-(1→ and →3,6)-α-D-GlcpA-(1→; δ99.51/4.44 can be attributed to →4)-α-D-Glcp-(1→ and →3,6)-α-D-GlcpA-(1→; δ98.6/3.6 can be attributed to α-D-Glcp-(1→ and →4)-α-D-Glcp-(1→.

All of the glycosidic bond signals of the polysaccharide are attributed by combining HMBC and NOESY, as shown in Table 1 below:

TABLE 1

Attribution of Hydrogen and Carbon Signals of IOP1-1 Component

| | Glycosyl residues | H1/C1 | H2/C2 | H3/C3 | H4/C4 | H5/C5 | H6a, b/C6 | H6b |
|---|---|---|---|---|---|---|---|---|
| A | →4)-α-D-Glcp(1→ | 5.32 | 3.52 | 3.86 | 3.6 | 4.12 | 3.3 | |
| | | 99.51 | 78.48 | 74.71 | 72.41 | 71.64 | 60.37 | |
| B | α-D-Glcp(1→ | 4.98 | 3.5 | 3.63 | 3.36 | 3.69 | 3.8 | 3.69 |
| | | 98.6 | 71.7 | 73.3 | 70.3 | 72.9 | 61.2 | |
| C | →6)-β-D-Glcp(1→ | 4.46 | 3.25 | 3.32 | 3.33 | 3.43 | 3.96 | 3.82 |
| | | 102.82 | 72.97 | 76.14 | 69.5 | 76.2 | 69.12 | |
| D | →4,6)-β-D-GlcpA(1→ | 4.68 | 3.6 | 3.89 | 3.7 | 3.33 | 3.63 | 3.64 |
| | | 101.29 | 73.52 | 74.52 | 77.75 | 70.61 | 70.52 | |
| E | →3)-α-D-Glcp(1→ | 5.169 | 3.94 | 4.058 | 4.25 | 4.36 | 3.7 | 3.7 |
| | | 97.9 | 67.75 | 80.07 | 69.28 | 70.78 | 61.64 | |
| F | →3,6)-α-D-GlcpA(1→ | 5.14 | 3.97 | 4.44 | 4.62 | 4.66 | 4.2 | 3.62 |
| | | 96.5 | 71 | 76.66 | 78.5 | 77.5 | 70.1 | |

Figure 9:
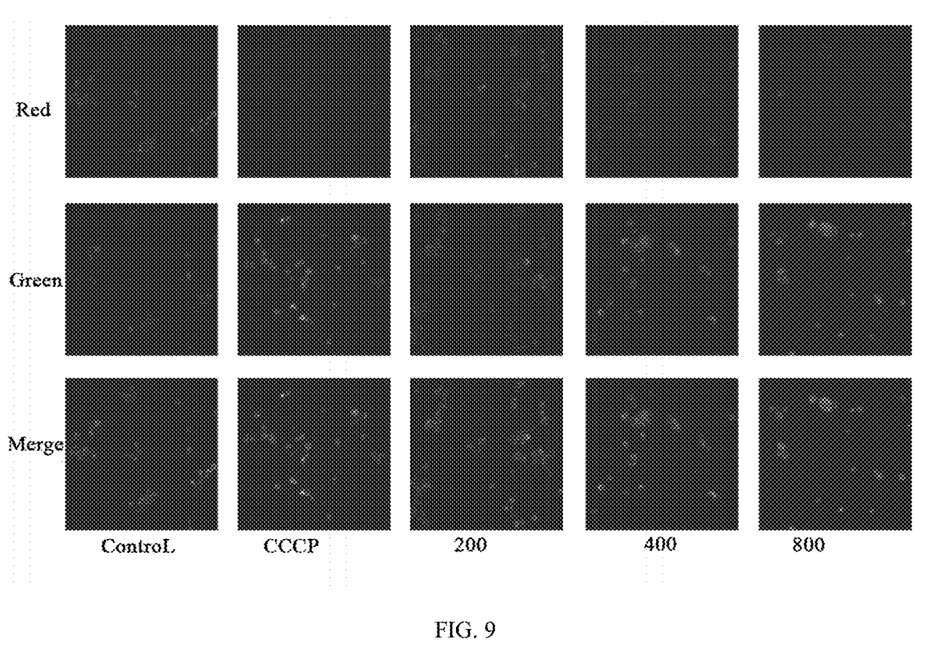
FIG. 9 shows mitochondrial membrane potential of AsPC-1 cell.

The *Inonotus Obliquus* polysaccharide prepared in this embodiment has structural formula as follows:

Embodiment 2 Antitumor Activity Experiment of *Inonotus Obliquus* Polysaccharide 1 Materials and Reagents 1.1 main reagent: RPMI-1640 culture medium, calf serum, trypsin and JC-10 detection kit of Solarbio Company; CCK-8 of Beyotime Company;

1.2 experimental cell line AsPC-1 of human metastatic pancreatic cancer is purchased from American Type Culture Collection (ATCC);

2 Methods 2.1 human metastatic pancreatic cancer cells are cultured in RPMI-1640 culture medium (containing penicillin 100 U/mL, streptomycin 100 U/mL and 10% fetal bovine serum) at 37° C. in a 5% $CO_2$ constant temperature incubator, and cells of logarithmic growth phase are taken for the experiment;

2.2 effect of *Inonotus Obliquus* polysaccharides on mitochondrial membrane potential: cells at logarithmic growth stage are inoculated in laser confocal cell culture dishes at a cell density of $1\times10^5$ pieces per milliliter (pcs/mL), and the culture medium is changed after 6 hours; *Inonotus Obliquus* polysaccharides prepared in Embodiment 1 of the present disclosure with different concentrations (0, 200 (microgram) per milliliter (μg/mL), 400 μg/mL, 800 ng/mL) are used to intervene the cells, and a positive control of carbonyl cyanide 3-chlorophenylhydrazone (CCCP) (10 mM) is also set; three dishes are set for each concentration, and the dishes are put in an incubator for incubation of 24 h after mixing evenly; the positive control group is treated with CCCP for 20 min in the incubator after aspirating the culture fluid, after which all dishes are treated and 1 mL of new culture fluid is added after aspirating out the culture fluids, then 1 mL of JC-10 staining working solution is added, followed by mixing well and incubating in the incubator for 20 min; after aspirating the culture fluid and washing the dishes twice with buffer, 2 mL of cell culture fluid is added and fluorescent observation is performed on a Leica LSM710/780 laser confocal microscope with photographs being taken, and the results as shown in FIG. 9 indicate that the mitochondrial membrane potential decreases as the concentration of drug administered increases, which is an early characteristic expression of apoptosis.

Therapeutic effects of two drugs, *Inonotus Obliquus* polysaccharide and gemcitabine hydrochloride, alone and in combination, on AsPC-1 (human metastatic pancreatic adenocarcinoma cells) cells are investigated respectively.

Cell culture: AsPC-1 (human metastatic pancreatic adenocarcinoma cells) cells are resuscitated in culture flasks and incubated at 37° C. in a 5% $CO_2$ incubator; the cells are adhered to the wall and then subjected to passaging or lyophilisation operations;

inoculation: when the cells are in logarithmic growth phase, they are washed twice with PBS buffer (phosphate concentration 0.01 M, pH 7.2-7.4); the cells are digested by 1 mL of 0.25% trypsin-EDTA (ethylene diamine tetraacetic acid) for 1-2 min, then 2 mL of RPMI-1640 culture solution containing 10% fetal bovine serum and 1% of double antibodies (penicillin and streptomycin) is added to terminate the digestion, followed by centrifuging at 1,000 revolutions per minute (rpm) for 3 min; then the wall-adhered cells are completely blown down and enumerated by hemocytometer plates, where the cells are inoculated in an 96-well plate in an amount of 100 μL per well, with a controlled number of 5,000 cells per well, and incubated in an incubator for 24 h.

Figure 10:
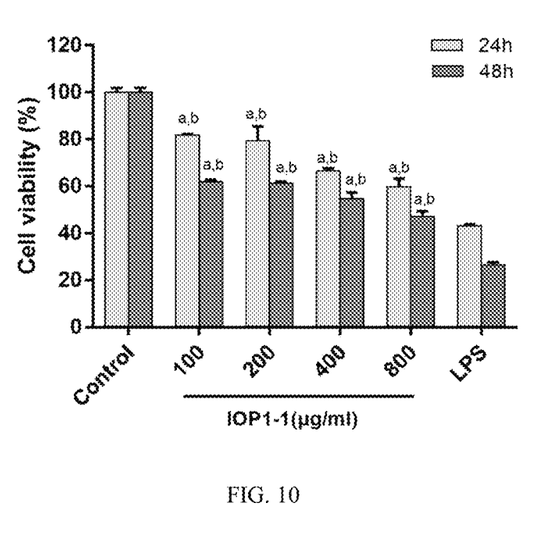
FIG. 10 shows proliferation of AsPC-1 cells.

CCK-8 experiment dosing: *Inonotus Obliquus* polysaccharide (IOP1-1) and lipopolysaccharide (LPS) are dissolved and diluted with RPMI-1640 culture solution to obtain different concentrations of drugs and combination solutions thereof, where the LPS solution is in a concentration of 2 μg/mL; the solutions of different groups are added to the corresponding wells of 96-well plates, and three replicate wells are set up for each group, a blank group without cells and drugs and a control group without drugs are set up; after 24 h of treatment, the medium of each group is discarded and replaced, and each well is then added with 10 μL of CCK-8 reagent and shaken well, followed by incubation in an incubator for 2 h; an enzyme marker is used to measure the absorbance at 450 nm and the results are shown in FIG. 10.

Calculation of cell viability for each group:Cell viability (%)=$(OD_{sample}-OD_{blank})\times100/(OD_{control}-OD_{blank})$ The cell viability of AsPC-1 cells treated with different concentrations of *Inonotus Obliquus* polysaccharide and gemcitabine hydrochloride and their combinations is shown in Table 2 below:

TABLE 2

Cell viability of AsPC-1 treated with different concentrations of IOP1-1 and gemcitabine hydrochloride and their combinations (n = 3)

| Drug combination | Cell vitality (%) |
|---|---|
| 0 μg/mL IOP1-1 + 0 μg/mL gemcitabine hydrochloride | 100 ± 0.41 |
| 0 μg/mL IOP1-1 + 20 μg/mL gemcitabine hydrochloride | 66.1 ± 5.49 |
| 400 μg/mL iop1-1 + 0 μg/mL gemcitabine hydrochloride | 78.2 ± 2.24 |
| 800 μg/mL iop1-1 + 0 μg/mL gemcitabine hydrochloride | 66.5 ± 4.12 |
| 400 μg/mL IOP1-1 + 20 μg/mL g/mL gemcitabine hydrochloride | 62.8 ± 16.84 |
| 800 μg/mL IOP1-1 + 20 μg/mL g/mL gemcitabine hydrochloride | 39.1 ± 3.96 |

As shown in Table 2, the therapeutic effect of the polysaccharide fraction on AsPC-1 tumor cells is excellent, and the effect of the combination of IOP1-1 and gemcitabine hydrochloride on tumor inhibition is even better, with 800 μg/mL IOP1-1+20 μg/mL gemcitabine hydrochloride having a synergistic effect in inhibiting ASPC-1 cells, enabling a reduction in the dosage of chemotherapeutic drugs and reducing the adverse effects of chemotherapeutic drugs.

The above-mentioned embodiments only describe the preferred mode of the disclosure, but do not limit the scope of the disclosure. On the premise of not departing from the design spirit of the disclosure, all kinds of modifications and improvements made by ordinary technicians in the field to the technical scheme of the disclosure shall fall within the scope of protection determined by the claims of the disclosure.

What is claimed is:

1. An application of an *Inonotus Obliquus* dextran in preparing drugs for treating human pancreatic cancer, comprising a method for preparing the *Inonotus Obliquus* dextran as follows:

(1) extracting *Inonotus Obliquus* crude polysaccharide from *Inonotus Obliquus* fruiting body by a water-extraction and alcohol-precipitation method;

(2) deproteinizing the *Inonotus Obliquus* crude polysaccharide in the step (1) by solvent extraction, followed by separation of components with molecular weight above 3,500 Dalton (Da) by dialysis to obtain a deproteinized crude sugar;

(3) purifying the deproteinized crude sugar by a DEAE-52 (Diethylaminoethyl) cellulose column to obtain a purified *Inonotus Obliquus* polysaccharide; and (4) placing the purified *Inonotus Obliquus* polysaccharide on a Sephadex G-100 gel column and eluting the purified *Inonotus Obliquus* polysaccharide with distilled water at a controlled flow rate of 0.5 milliliter per minute (mL/min) to obtain the *Inonotus Obliquus* dextran;

wherein the purifying in the step (3) specifically comprises: dissolving the deproteinized crude sugar in water, followed by loading onto the DEAE-52 cellulose chromatographic column; then performing fractional elution with distilled water, 0.05 mole per liter (mol/L) NaCl, 0.1 mol/L NaCl and 0.2 mol/L NaCl respectively under a controlled flow rate of 1.0 mL/min, separately collecting eluents and combining polysaccharide elution sites to obtain purified *Inonotus Obliquus* polysaccharide; and the *Inonotus Obliquus* dextran is in a molecular weight of 6.886 Kilodalton (kDa).

2. The application according to claim 1, wherein in the step (1), the water-extraction and alcohol-precipitation method comprises: leaching the *Inonotus Obliquus* fruiting body with deionized water to obtain a leaching solution, concentrating the leaching solution, and adding ethanol to obtain the *Inonotus Obliquus* crude polysaccharide by precipitation.

3. The application according to claim 1, wherein the solvent extraction in the step (2) uses Sevage reagent prepared with n-butanol and chloroform in a volume ratio of 1:4.

* * * * *